United States Patent [19]

Sommer et al.

[11] Patent Number: 4,985,415
[45] Date of Patent: Jan. 15, 1991

[54] PESTICIDAL THIONOPHOSPHONIC ACID(AMIDE) ESTERS

[75] Inventors: Herbert Sommer, Remscheid; Dieter Arlt, Cologne; Jürgen Hartwig, Leverkusen; Bernhard Homeyer, Leverkusen; Hans-Detlef Matthaei, Leverkusen, all of Fed. Rep. of Germany

[73] Assignee: Bayer Aktiengesellschaft, Leverkusen, Fed. Rep. of Germany

[21] Appl. No.: 327,650

[22] Filed: Mar. 23, 1989

[30] Foreign Application Priority Data

Mar. 31, 1988 [DE] Fed. Rep. of Germany ....... 3811004

[51] Int. Cl.$^5$ .......................... A01N 9/36; C07F 9/02
[52] U.S. Cl. ..................................... 514/118; 558/199
[58] Field of Search .......................... 558/199; 514/118

[56] References Cited

U.S. PATENT DOCUMENTS 4,104,377 8/1978 Arlt et al. ............................ 558/204
4,159,324 6/1979 Arlt et al. ............................ 558/199

FOREIGN PATENT DOCUMENTS 2528996 1/1977 Fed. Rep. of Germany .
2630561 1/1978 Fed. Rep. of Germany .

*Primary Examiner*—Cecilia Shen
*Attorney, Agent, or Firm*—Sprung Horn Kramer & Woods

[57] ABSTRACT

Pesticidal thionophosphonic acid(amide) esters of the formula

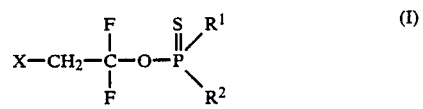

in which
$R^1$ stands for optionally substituted alkyl or alkenyl,
$R^2$ stands for optionally substituted alkoxy, alkenyloxy or alkinyloxy, or for the group

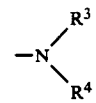

in which
$R^3$ and $R^4$ are identical or different and independently of one another stand for hydrogen or for optionally substituted alkyl, cycloalkyl, alkenyl or alkinyl, or together with the nitrogen atom form a 5- to 7-membered, saturated or unsaturated ring and
X stands for halogen.
Intermediates of the formuula

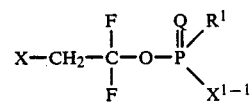

are also new.

13 Claims, No Drawings

PESTICIDAL THIONOPHOSPHONIC ACID(AMIDE) ESTERS

The invention relates to new thionophosphonic acid-(amide) esters, a process for their preparation, their use as pesticides, in particular as insecticides, acaricides and nematicides, and new intermediates and a process for the preparation of such intermediates.

It has already been disclosed that certain thionophosphoric(phosphonic) acid amide esters, such as, for example, O-methyl O-(2-chloro-1-fluoro-ethyl) thionophosphoramidate, have a pesticidal action (cf. DE-OS (German Published Specification) 2,629,016, or the corresponding U.S. Pat. No. 4,159,324). However, the action and the duration of action of these known compounds are not always completely satisfactory, in particular at low application rates and when low concentrations of active compound are used.

New thionophosphonic acid(amide) esters of the general formula $$\begin{array}{c} F \quad\quad S \quad R^1 \\ | \quad\quad \| / \\ X-CH_2-C-O-P \\ | \quad\quad\quad \backslash \\ F \quad\quad\quad R^2 \end{array} \quad (I)$$

have now been found, in which formula $R^1$ stands for optionally substituted radicals from the series comprising alkyl and alkenyl, $R^2$ stands for optionally substituted radicals from the series alkoxy, alkenyloxy, alkinyloxy or for the group $$-N\begin{array}{c}R^3 \\ \backslash R^4\end{array}$$

in which $R^3$ and $R^4$ are identical or different and independently of one another stand for hydrogen and for optionally substituted radicals from the series comprising alkyl, cycloalkyl, alkenyl or alkinyl, or together with the nitrogen atom form a 5- to 7-membered, saturated or unsaturated ring and X stands for halogen.

The compounds of the formula (I) possess an asymmetrically substituted phosphorus atom and if appropriate an asymmetrically substituted carbon atom. Thus, they can be present in different optical isomer forms, which can be obtained in amounts of various ratios. In all cases, they are mainly present as racemates. The invention relates both to the isomer mixtures and to the individual isomers.

Furthermore, it has been found that the new thionophosphonic acid(amide) esters of the formula (I) are obtained in a process in which O-(1,1-difluoro-2-halogeno-ethyl) halogenothionophosphonates of the formula $$\begin{array}{c} F \quad\quad S \quad R^1 \\ | \quad\quad \| / \\ X-CH_2-C-O-P \\ | \quad\quad\quad \backslash \\ F \quad\quad\quad X^{1-1} \end{array} \quad (II)$$

in which

X and $R^1$ have the abovementioned meaning and $X^{1-1}$ stands for halogen, preferably chlorine, (a) are reacted with amines of the formula $$HN\begin{array}{c}R^3 \\ \backslash R^4\end{array} \quad (III)$$

in which $R^3$ and $R^4$ have the abovementioned meaning, if appropriate in the presence of a diluent and if appropriate in the presence of an acid acceptor, or (b) are reacted with alcohols of the formula $$R^{1-1}-M \quad (IV)$$

in which $R^{2-1}$ stands for optionally substituted radicals from the series comprising alkoxy, alkenyloxy and alkinyloxy and M stands for hydrogen or an alkali metal equivalent or alkaline earth metal equivalent, if appropriate in the presence of a diluent and if appropriate in the presence of an acid acceptor.

The new thionophosphonic acid(amide) esters of the formula (I) are distinguished in an outstanding manner by a particularly high activity as pesticides, in particular as insecticides, acaricides and nematicides.

The substances according to the invention thus represent a valuable enrichment of the art.

Optionally substituted alkyl in the definition of $R^1$, $R^3$ and $R^4$ in the general formulae stands for straight-chain or branched alkyl having preferably 1 to 20, particularly preferably 1 to 12, in particular 1 to 6 and very particularly preferably 1 to 4, carbon atoms. Optionally substituted methyl, ethyl, n-propyl, i-propyl, n-butyl, sec-butyl, i-butyl, tert-butyl, n-pentyl, i-pentyl and tert-pentyl may be mentioned as examples.

Straight-chain or branched alkenyl having preferably 2 to 8, particularly preferably 2 to 6 and in particular 2 to 4, carbon atoms stands for the term optionally substituted alkenyl itself or as a component of the group alkenyloxy in the definitions of $R^1$, $R^2$, $R^{2-1}$, $R^3$ and $R^4$ in the general formulae. Optionally substituted vinyl, allyl, 2-butenyl, 3-butenyl and 1-methallyl may be mentioned as examples.

The term optionally substituted alkoxy in the definitions $R^2$ and $R^{2-1}$ in the general formulae is taken to mean straight-chain or branched alkoxy having preferably 1 to 6, in particular 1 to 4, carbon atoms. Optionally substituted methoxy, ethoxy, propoxy, butoxy and their isomers, such as, for example, i-propoxy, i-, s- and tert.-butoxy, may be mentioned as examples, with the particular emphasis on optionally substituted methoxy and ethoxy.

The term optionally substituted alkinyl itself or as a component of the group alkinyloxy in the definitions $R^2$, $R^{2-1}$, $R^3$ and $R^4$ in the general formulae is taken to mean straight-chain or branched alkinyl having preferably 2 to 6, in particular 2 to 4, carbon atoms. Optionally substituted ethinyl, 2-propinyl, 2-butinyl, 3-butinyl and 1-methyl-2-propinyl may be mentioned as examples.

Optionally substituted cycloalkyl in the definitions $R^2$ and $R^3$ stands for cycloalkyl having preferably 3 to 8, in particular 3, 5 or 6, carbon atoms. Optionally substituted cyclopropyl, cyclobutyl, cyclopentyl, cyclohexyl and cycloheptyl may be mentioned as examples.

The substituted radicals mentioned in the definition of $R^1$, $R^2$, $R^{2-1}$, $R^3$ and $R^4$ can carry one or more, preferably 1 to 3, in particular 1 or 2, identical or different substituents. Preferred substituents for alkyl, alkenyl and alkinyl which may be listed are alkoxy having 1 to 4 carbon atoms, such as methoxy, ethoxy, n-propoxy, i-propoxy, n-butoxy, i-butoxy, sec-butoxy, tert-butoxy and halogen.

The radicals alkoxy, alkenyloxy and alkunyloxy, when substituted, are preferably substituted by halogens, such as fluorine, chlorine, bromine and iodine, in particular fluorine, chlorine and bromine, and $C_1$–$C_4$-alkoxy.

Preferred substituents for cycloalkyl Qhich may be listed are alkyl having 1 to 4 carbon atoms, such as methyl, ethyl, n-propyl, i-propyl, n-butyl, i-butyl, sec-butyl and tert-butyl, halogenoalkyl, such as, for example, trifluoromethyl and halogen.

Halogen, in the definition X and $X^{1-1}$ in the general formulae and as substituents for a group, stands for fluorine, chlorine, bromine and iodine, in particular fluorine, chlorine and bromine, in the case of X halogen preferably denoting chlorine and bromine and in the case of $X^{1-1}$ halogen preferably standing for chlorine.

When $R^2$ and $R^3$ together with the nitrogen atom form a ring, the latter contains 5 to 7, preferably 5 or 6, ring members. The ring can contain 1 to 3 double bonds; preferably, however, it is saturated. Particularly preferred rings which may be mentioned are the pyrrolidine and the piperidine ring.

In the general formulae, $R^1$ preferably stands to $C_1$–$C_4$-alkyl, in particular for methyl and ethyl.

In the general formulae, $R^2$ preferably stands for $C_1$–$C_4$-alkoxy, in particular methoxy and ethoxy.

In the compounds in which $R^2$ stands for the —$NR^3R^4$ group, one of the radicals $R^3$ and $R^4$ preferably denotes hydrogen. $R^3$ particularly preferably stands for hydrogen and $R^4$ for $C_1$–$C_4$-alkyl or for $C_2$–$C_4$-alkenyl.

Halogen X preferably denotes chlorine or bromine.

The radicals $R^1$, $R^2$, $R^3$ and $R^4$ are preferably unsubstituted.

Preferred thionophosphonic acid(amide) esters of the formula (I) according to the invention are those in which $R^1$ stands for $C_1$–$C_4$-alkyl and $C_2$–$C_4$-alkenyl, each of which is optionally substituted by halogen, $R^2$ stands for $C_1$–$C_4$-alkoxy, $C_2$–$C_4$-alkenyloxy and $C_2$–$C_4$-alkinyloxy, each of which is optionally substituted by halogen and/or $C_1$–$C_4$-alkoxy, or for the group $$-N\begin{matrix}R^3\\R^4\end{matrix}$$

in which $R^3$ and $R^4$ are identical or different and independently of one another stand for hydrogen, for $C_1$–$C_4$-alkyl which is optionally substituted by halogen and/or $C_1$–$C_4$-alkoxy; for cycloalkyl which has 3 to 8 carbon atoms and which is optionally substituted by methyl, ethyl, fluorine and/or chlorine; for $C_2$–$C_4$-alkenyl and $C_2$–$C_4$-alkinyl, each of which is optionally substituted by halogen, methyl and/or ethyl, or together with the nitrogen atom form a 5- or 6-membered, saturated or unsaturated ring and X stands for fluorine, chlorine or bromine. Particularly preferred compounds among these are those in which $R^1$ stands for $C_1$–$C_4$-alkyl which is optionally substituted by halogen, $R^2$ stands for $C_1$–$C_4$-alkoxy which is optionally substituted by halogen or $C_1$–$C_4$-alkoxy, or for the group $$-N\begin{matrix}R^3\\R^4\end{matrix}$$

in which $R^3$ and $R^4$ are identical or different and stand for hydrogen or for $C_1$–$C_4$-alkyl which is optionally substituted by halogen or $C_1$–$C_4$-alkoxy (with preferably one of the radicals denoting hydrogen) and X stands for chlorine or bromine.

Particularly preferred thionophosphonic acid (amide) esters of the formula (I) are those in which $R^1$ stands for $C_1$–$C_2$-alkyl and $C_2$–$C_3$-alkenyl, each of which is optionally substituted by fluorine and/or chlorine, $R^2$ stands for $C_1$–$C_4$-alkoxy, $C_2$–$C_3$-alkenyloxy or $C_2$–$C_3$-alkinyloxy, each of which is optionally substituted by fluorine, chlorine, methoxy and/or ethoxy, or for the group $$-N\begin{matrix}R^3\\R^4\end{matrix}$$

in which $R^3$ and $R^4$ are identical or different and independently of one another stand for hydrogen, for $C_1$–$C_4$-alkyl which is optionally substituted by fluorine, chlorine, bromine, methoxy and/or ethoxy, for cycloalkyl which has 3 to 6 carbon atoms and which is optionally substituted by methyl, ethyl, fluorine and/or chlorine; for $C_2$–$C_4$-alkenyl and $C_2$–$C_4$-alkinyl, each of which is optionally substituted by fluorine, chlorine, methyl and/or ethyl, or together with the nitrogen atom to which they are bonded stand for piperidyl and pyrrolidinyl and X stands for fluorine, chlorine and bromine.

Very particularly preferred thionophosphonic acid (amide) esters of the formula (I) are those in which $R^1$ stands for methyl and ethyl, $R^2$ stands for methoxy, ethoxy, methylamino, ethylamino, n- and iso-propylamino, sec-butylamino, diethylamino or allylamino and X stands for chlorine and bromine.

If, for example, O-(2-chloro-1,1-difluoro-ethyl) ethanechlorothionophosphonate and n-propylamine are used as starting substances, the course of the reaction of the process according to the invention can be represented by the following equation:

$$\text{Cl}-\text{CH}_2-\underset{\underset{F}{|}}{\overset{\overset{F}{|}}{C}}-\text{O}-\overset{\overset{S}{\|}}{\underset{\underset{Cl}{\diagdown}}{P}}\diagup^{C_2H_5} + \text{CH}_3-\text{CH}_2-\text{CH}_2-\text{NH}_2 \longrightarrow$$

-continued

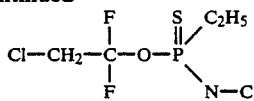

If, for example, O-(2-chloro-1,1-difluoro-ethyl) ethanechlorothionophosphonate and sodium ethoxide are used as starting substances, the course of the reaction of the process according to the invention can be represented by the following equation:

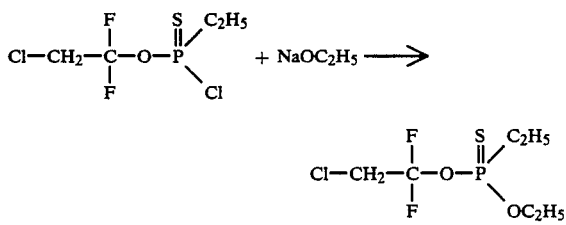

Formula (II) provides a general definition of the O-(1,1-difluoro-2-halogeno-ethyl) halogenothionophosphonates to be used as starting substances in the process according to the invention. In this formula (II), X, $X^{1-1}$ and $R^1$ preferably, or particularly preferably stand for those radicals which are mentioned above in the definitions of the formulae (I) and (II).

The O-(1,1-difluoro-2-halogeno-ethyl) halogenothionophosphonates of the formula (II) are new and form part of the present invention.

The compounds of the formula (II) are obtained when O-(1,1-difluoro-2-halogeno-ethyl) halogenophosphonates of the formula

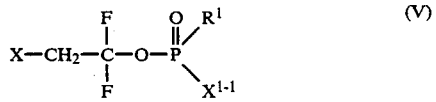

in which

X, $X^{1-1}$ and $R^1$ have the abovementioned meaning, are reacted with thiophosphoryl chloride of the formula

if appropriate in the presence of a diluent and if appropriate in the presence of a phosphorus sulphide, such as, for example, phosphorus(V) sulphide ($P_2S_5$, $P_4S_{10}$) or 2,4-bis-(4-methoxyphenyl)-1,3,2,4-dithiadiphosphetane 2,4-disulphide (Lawesson's reagent).

Formula (V) provides a general definition of the O-(1,1-difluoro-2-halogeno-ethyl) halogenophosphonates to be used as starting substances. In this formula (V), $R^1$, X and $X^{1-1}$ preferably, or particularly preferably, stand for those radicals which are mentioned above in the definitions of formula (I).

The compounds of the formula (V) are new, but they can be prepared by processes and methods known from the literature (cf. DE-OS (German Published Specification) 2,528,996).

Thiophosphoryl chloride of the formula (VI) ($PSCl_3$), which is also to be used as starting substance, is a generally known compound of inorganic chemistry.

Suitable diluents for preparing the new compounds of the formula (II) are virtually inert organic solvents, and also thiophosphoryl chloride.

These preferably include aromatic, optionally halogenated hydrocarbons, such as toluene, xylene, chlorobenzene, o-dichlorobenzene, dichlorotoluene and mono- or dichloroxylene. Thiophosphoryl chloride is particularly preferred.

The process according to the invention for the preparation of the new compounds of the formula (II) is generally carried out at temperatures between 100° C. and 160° C., preferably at temperatures between 120° C. and 140° C.

When carrying out the process according to the invention for the preparation of the compounds of the formula (II), 1 mol of starting substance of the formula (V) is reacted with 1 to 20 mols, preferably 1 to 6 mols, of thiophosphoryl chloride and 0.0001 to 0.2 mol, preferably 0.001 to 0.01 mol, of phosphorus(V) sulphide. The reactions are generally carried out under atmospheric pressure.

When carrying out the process according to the invention for the preparation of the compounds of the general formula (II), the starting substance of the formula (V) is boiled to reflux together with phosphorus(V) sulphide in one of the stated solvents, particularly preferably thiophosphoryl chloride, with the phosphorus oxychloride formed being continuously distilled off. When the reaction is complete, the compounds of the formula (II), which are obtained as crude products, can be purified in a conventional manner, advantageously by fractional distillation under reduced pressure. They are characterized by the retention index (Kovats index).

The process according to the invention for the preparation of the new compounds of the formula (I) is preferably carried out using diluents.

These preferably include aliphatic or aromatic, optionally halogenated hydrocarbons, such as, for example, pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as dimethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in the process for the preparation of the new compounds of the formula (I) are all the acid-binding agents which can generally be used for reactions of this type. Alkaline earth metal hydroxides, such as, for example, calcium hydroxide, alkali metal carbonates and alkali metal alkoxides, such as sodium carbonate and potassium carbonate, sodium methoxide, potassium methoxide, sodium ethoxide and potassium ethoxide, furthermore aliphatic, aromatic or heterocyclic amines, for example triethylamine, trimethylamine, dimethylaniline, dimethylbenzylamine, pyridine, collidine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferably suitable.

When carrying out the process for the preparation of the compounds of the formula (I), the reaction temperatures can be varied within a relatively wide range. In general, the process is carried out at temperatures between 0° C. and 100° C., preferably at temperatures between 20° C. and 60° C.

In general, the reaction is allowed to proceed under atmospheric pressure. For carrying out the process according to the invention, the reactants are preferably employed in the equimolar ratio. An excess of one or the other component does not provide any essential advantages. The reaction is preferably carried out in one of the stated solvents in the presence of an acid acceptor. Working up of the batch is carried out by customary methods, by filtration, washing of the filtrate and distilling off the solvent.

The new compounds are obtained in the form of oils, some of which cannot be distilled without decomposition, but can be freed from the last volatile constituents by so-called "incipient distillation", i.e. by heating under reduced pressure for a relatively long time to a moderately elevated temperature, and can be purified in this manner. They are characterized by the retention index (Kovats index).

The active compounds are suitable for combating animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix, Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, *Eurygaster* spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., Trichoplusia ni, Carpocapsa pomonella, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus,* Acanthoscelides obtectus, Hylotrupes bajulus, Agelastica alni, Leptinotarsa decemlineata, Phaedon cochleariae, Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp , Ixodes spp., Psoroptes spp., Chorioptes spp., Sarcoptes spp., Tarsonemus spp., *Bryobia praetiosa,* anonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds of the formula (I) according to the invention are distinguished by an excellent insecticidal activity. In particular when employed as soil insecticides, they show an excellent action against grubs, such as, for example, *Porbia antiqua* grubs, against aphids, such as, for example *Myzus persicae* and *Aphis fabae,* and also an excellent action against nematodes, such as, for example, *Meliodogyne incognita.*

The active compounds according to the invention are distinguished by an excellent insecticidal activity, in particular in the combating of Orthoptera species, such as, for example, *Blattella germanica* and Coleoptera species, such as, for example, *Sitophilus granarius.*

The active compounds according to the invention can also be employed with very good success for combating hygiene pests, such as, for example, *Musca do-*

*mestica* Diptera *Aedes aegypti* Diptera and *Aedes aegypti larvae*. Some of the active compounds according to the invention also show a leaf-acting insecticidal action.

Depending on their respective physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable, for example, ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable, for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable, for example, non-ionic and anionic emulsifiers, such as polyoxyethylene-fatty acid esters, polyoxyethylene-fatty alcohol ethers, for example alkylaryl polyglycol ethers, alkylsulphonates, alkyl sulphates and sulphates and arylsulphonates as well as albumin hydrolysis products; as dispersing agents there are suitable, for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES:

Example I-1

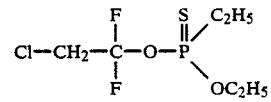

10.2 g of a 20% strength sodium ethoxide solution (0.03 mol) are added dropwise at 0° C. to a solution of 7.3 g (0.03 mol) of O-(2-chloro-1,1-difluoro-ethyl) ethanechlorothionophosphonate in 50 ml of toluene, and the mixture is stirred for 4 hours at room temperature. It is then evaporated, the residue is taken up in toluene, the mixture is washed twice with water, the organic phase is dried, the solvent is stripped off, and the residue is distilled using a bulb tube.

O-Ethyl O-(2-chloro-1,1-difluoro-ethyl) ethanethionophosphonate of retention index 1223* is obtained in 36% yield.

Example I-2

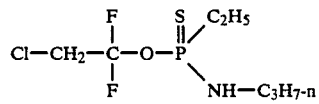

3.6 g (0.06 mol) of n-propylamine are added dropwise at room temperature to a solution of 7.3 g (0.03 mol) of O-(2-chloro-1,1-difluoro-ethyl) ethanechlorothionophosphonate in 50 ml of toluene. The reaction mixture is washed twice with water, the organic phase is separated off and dried over magnesium sulphate, and the toluene is stripped off under reduced pressure.

3.5 g (66% of theory) of O-(2-chloro-1,1-difluoroethyl) propylamidoethanethionophosphonate of retention index 1461* are obtained.

The end products of the formula

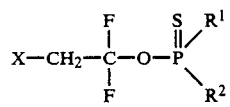

which are listed in Table 1 below are obtained analogously to Example (I-1) and (I-2) and taking into consideration the instructions in the description of the process according to the invention:

TABLE 1

| Example No. | X | R¹ | R² | Retention Index* |
|---|---|---|---|---|
| I-3 | Cl | -C₂H₅ | -NH-C₃H₇-iso | 1397 |
| I-4 | Cl | —C₂H₅ | —OCH₃ | 1161 |
| I-5 | Cl | —C₃ | —OCH₃ | 1081 |
| I-6 | Cl | —CH₃ | —NH—C₃H₇-iso | 1325 |
| I-7 | Cl | —CH₃ | —OC₂H₅ | 1141 |
| I-8 | Cl | —CH₃ | —NH—CH₂—CH=CH₂ | 1369 |
| I-9 | Cl | —CH₃ | —N(C₂H₅)₂ | 1387 |
| I-10 | Cl | —CH₃ | —NH—C₃H₇-n | 1384 |
| I-11 | Cl | —C₂H₅ | —N(C₂H₅)₂ | 1469 |
| I-12 | Cl | —C₂H₅ | —NH—CH₂—CH=CH₂ | 1443 |
| I-13 | Cl | —C₂H₅ | —NH—C₂H₅ | 1372 |
| I-14 | Br | —C₂H₅ | —NH—C₄H₉-sec | 1578 |
| I-15 | Br | —C₂H₅ | —NH—C₃H₇-iso | 1485 |
| I-16 | Br | —C₂H₅ | —OCH₃ | 1249 |
| I-17 | Br | —C₂H₅ | —OC₂H₅ | 1301 |
| I-18 | Br | —C₂H₅ | —N(C₂H₅)₂ | 1548 |
| I-19 | Cl | —C₂H₅ | —NH—C₄H₉-sec. | 1496 |

* The retention indices (Kovats index) were determined on a boiling point phase (dimethylsilicone) by means of gas chromatography.

PREPARATION OF STARTING MATERIALS

Example (II-1)

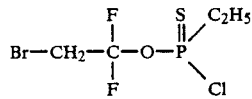

581 g (2.14 mol) of O-(2-bromo-1,1-difluoroethyl) ethanechlorophosphonate, 1303 g (7.7 mol) of thiophosphoryl chloride and 13.1 g (0.06 mol) of phosphorus (V) sulphide are heated for 5 days to 140° C. bath temperature and then distilled.

566 g (92% of theory) of O-(2-bromo-1,1-difluoroethyl) ethanechlorothionophosphonate of boiling point 61° C./0.7 mbar of retention index 1242* are obtained.

The compounds of the formula

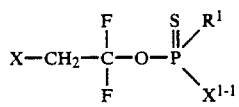

which are listed in Table 2 below are also obtained by the method indicated in Example (II-1):

| Example No. | X | R¹ | X¹⁻¹ | Retention Index* |
|---|---|---|---|---|
| II-2 | Cl | —CH₃ | Cl | 1078 |
| II-3 | Cl | —C₂H₅ | Cl | 1159 |

* The retention indices (Kovats index) were determined on a boiling point phase (dimethylsilicone) by means of gas chromatography.

USE EXAMPLES

In the subsequent Use Examples, the compound indicated below has been employed as comparison compound:

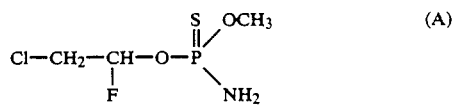

(disclosed in DE-OS (German Published Specification) 2,629,016, or the corresponding U.S. Pat. No. 4,159,324).

Example A

Test insect: *Phorbia antiqua* maggots (in the soil).
Solvent: 3 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example the compounds of the Preparation Examples I-3, I-4, I-1, I-6, I-10, I-12, I-13 and I-2 show a degree of destruction of 100% at an exemplary concentration of 20 ppm, while the comparison compound resulted in a degree of destruction of 0% at the same concentration.

Example B

Root-systemic action

Test insect: *Myzus persicae.*
Solvent: 3 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all test insects have been killed and 0% if just as many test insects are still alive as in the case of the untreated control.

In this test, for example the compound of Preparation Example I-2 showed a destruction figure of 95% at an exemplary concentration of 10 ppm, while the comparison compound resulted in the destruction of 0% at the same concentration.

Example C

Test nematode: *Meloidogyne incognita*.
Solvent: 3 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is filled into pots, lettuce is sown and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example the compounds of Preparation Examples I-13 and I-2 showed a degree of effectiveness of 95–100% at an exemplary concentration of 2.5 ppm, while the comparison compound resulted in a degree of effectiveness of 0% at the same concentration.

Example D $LT_{100}$ test for Diptera

Test insects: *Musca domestica*.
Number of test insects 25.
Solvent: acetone.

2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The condition of the test insects is checked continuously. The time required for a 100% knock-down effect is determined.

In this test, for example the compounds of Preparation Examples I-3, I-1, I-6, I-12, I-13 and I-2 showed an $LT_{100}$ of 25' to 50' at an exemplary concentration of 0.02%, while the comparison compound resulted in an $LT_{100}$ of 90' at the same concentration.

Example E

Test insects: *Blattella germanica*.
Solvent: acetone.

2 parts by weight of active compound are taken up in 1,000 parts by volume of solvent. The solution thus obtained is diluted with further solvent to the desired concentration.

2.5 ml of the active compound solution are pipetted into a Petri dish. A filter paper disc of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, for example the compounds of Preparation Examples I-3, I-4, I-1, I-6, I-8, I-12, I-13 and I-2 showed a destruction of 100% at an exemplary concentration of 0.002%, while the comparison compound resulted in the destruction of 60% at the same concentration.

Example F

Test insects: *Sitophilus granarius*.
Solvent: acetone.

2 parts by weight of active compound are taken up in 1,000 parts by volume of solvent. The solution thus obtained is diluted with further solvent to the desired concentration.

2.5 ml of the active compound solution are pipetted into a Petri dish. A filter paper disc of about 9.5 cm diameter is located on the bottom of the Petri dish. The Petri dish is left standing open until the solvent has completely evaporated. The amount of active compound per m² of filter paper varies, depending on the concentration of the active compound solution. A number of test insects is then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, for example the compounds of Preparation Examples I-3, I-4, I-1, I-6, I-8, I-12, I-13 and I-2 showed a destruction of 100% at an exemplary concentration of 0.002%, while the comparison compound resulted in the destruction of 30% at the same concentration.

Example G

LT$_{100}$ test for Diptera

Test insects: *Aedes aegypti.*
Solvent: acetone.

2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m$^2$ of filter paper varies, depending on the concentration of the active compound solution. The stated number of test insects is then introduced into the Petri dish, and the dish is covered with a glass lid.

The condition of the test insects is checked continuously. The time required for a 100% knock-down effect is determined.

In this test, for example the compounds of Preparation Examples I-3, I-5, I-6, I-8, I-12, I-13 and I-2 showed an LT$_{100}$ of 60′ to 120′ at an exemplary concentration of 0.002%, while the comparison compound resulted in an LT$_{100}$ of 3$^h$ (50%) at the same concentration.

Example H

Mosquito larvae test

Test insects: *Aedes aegypti.*
Solvent: 99 parts by weight of acetone.
Emulsifier: 1 part by weight of benzylhydroxybiphenyl polyglycol ether.

To produce a suitable preparation of active compound, 2 parts by weight of active compound are dissolved in 1,000 parts by volume of the solvent, containing the amount of emulsifier stated above. The solution thus obtained is diluted with water to the desired lower concentrations.

The aqueous preparations of active compound of the desired concentration are filled into glass vessels and about 25 mosquito larvae are then placed in each glass vessel.

After 24 hours, the degree of destruction in % is determined. 100% means that all larvae have been killed. 0% means that no larvae at all have been killed.

In this test, for example the compounds of Preparation Examples I-3, I-4, I-1, I-6, I-8, I-12, I-13 and I-2 showed a degree of destruction of 100% at en exemplary concentration of 1%, while the comparison compound resulted in a degree of destruction of 0% at the same concentration.

It will be appreciated that the instant specification and claims are set forth by way of illustration and not limitation, and that various modifications and changes may be made without departing from the spirit and scope of the present invention.

What is claimed is:

1. An O-(1,1-difluoro-2-halogeno-ethyl) halogenothionophosphonate of the formula $$X-CH_2-\underset{\underset{F}{|}}{\overset{\overset{F}{|}}{C}}-O-\underset{\underset{X^{1-1}}{\diagdown}}{\overset{\overset{S}{\|}}{P}}\overset{R^1}{\diagup}$$

in which
R$^1$ stands for C$_1$-C$_4$-alkyl or C$_2$-C$_4$-alkenyl each of which is optionally substituted by halogen,
R$^2$ stands for C$_1$-C$_4$-alkoxy, C$_2$-C$_4$-alkenyloxy or C$_2$-C$_4$-alkinyloxy each of which is optionally substituted by halogen and/or C$_1$-C$_4$-alkoxy, or for the group $$-N\overset{R^3}{\underset{H}{\diagdown}}\diagup$$

in which
R$^3$ stands for C$_1$-C$_4$-alkyl which is optionally substituted by halogen and/or C$_1$-C$_4$-alkoxy; for cycloalkyl which has 3 to 8 carbon atoms and which is optionally substituted by methyl, ethyl, fluorine and/or chlorine; or for C$_2$-C$_4$-alkenyl or C$_2$-C$_4$-alkinyl, each of which is optionally substituted by halogen, methyl and/or ethyl, and
X and X$^{1-1}$ each independently stands for halogen.

2. A thionophosphonic acid(amide) ester of the formula $$X-CH_2-\underset{\underset{F}{|}}{\overset{\overset{F}{|}}{C}}-O-\underset{\underset{R^2}{\diagdown}}{\overset{\overset{S}{\|}}{P}}\overset{R^1}{\diagup} \quad (I)$$

R$^1$ stands for C$_1$-C$_4$-alkyl or C$_2$-C$_4$-alkenyl each of which is optionally substituted by halogen,
R$^2$ stands for C$_1$-C$_4$-alkoxy, C$_2$-C$_4$-alkenyloxy or C$_2$-C$_4$-alkinyloxy each of which is optionally substituted by halogen and/or C$_1$-C$_4$-alkoxy, or for the group $$-N\overset{R^3}{\underset{H}{\diagdown}}\diagup$$

in which
R$^3$ stands for C$_1$-C$_4$-alkyl which is optionally substituted by halogen and/or C$_1$-C$_4$-alkoxy; for cycloalkyl which has 3 to 8 carbon atoms and which is optionally substituted by methyl, ethyl, fluorine and/or chlorine; or for C$_2$-C$_4$-alkenyl or C$_2$-C$_4$-alkinyl, each of which is optionally substituted by halogen, methyl and/or ethyl, and
X stands for fluorine, chlorine or bromine.

3. A thionophosphonic acid(amide) ester according to claim 2 in which
R$^1$ stands for C$_1$-C$_2$-alkyl or C$_2$-C$_3$-alkenyl, each of which is optionally substituted by fluorine and/or chlorine,
R$^2$ stands for C$_1$-C$_4$-alkoxy, C$_2$-C$_3$-alkenyloxy or C$_2$-C$_3$-alkinyloxy, each of which is optionally substituted by fluorine, chlorine, methoxy and/or ethoxy, or for the group

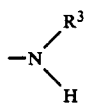

in which

R³ stands for C₁–C₄-alkyl which is optionally substituted by fluorine, chlorine, bromine, methoxy and/or ethoxy, for cycloalkyl which has 3 to 6 carbon atoms and which is optionally substituted by methyl, ethyl, fluorine and/or chlorine; for C₂–C₄-alkenyl or C₂–C₄-alkinyl, each of which is optionally substituted by fluorine, chlorine, methyl and/or ethyl, and X stands for fluorine, chlorine and bromine.

4. A thionophosphonic acid(amide) ester according to claim 2, in which

R¹ stands for methyl and ethyl,

R² stands for methoxy, ethoxy, methylamino, ethylamino, n- and iso-propylamino, sec-butylamino, diethylamino, allylamino and X stands for chlorine and bromine.

5. A compound according to claim 2, wherein such compound is O-ethyl O-(2-chloro-1,1-difluoro-ethyl)-ethanethionophosphonate of the formula

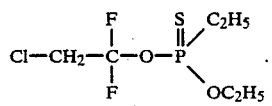

6. A compound according to claim 1, wherein such compound is O-(2-chloro-1,1-difluoro-ethyl) propylamidoethanethionophosphonate of the formula

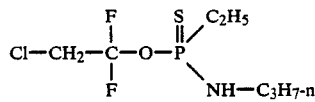

7. A compound according to claim 2, wherein such compound is O-(2-chloro-1,1-difluoro-ethyl) isopropylamidoethanethionophosphonate of the formula

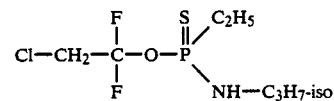

8. A compound according to claim 2, wherein such compound is O-(2-chloro-1,1-difluoro-ethyl) isopropylamidomethanethionophosphonate of the formula

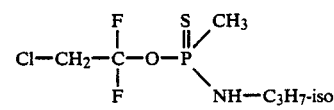

9. A compound according to claim 2, wherein such compound is O-(2-chloro-1,1-difluoro-ethyl) allylamidoethanethionophosphonate of the formula

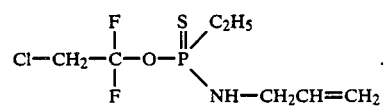

10. A compound according to claim 2, wherein such compound is O-(2-chloro-1,1-difluoro-ethyl) ethylamidoethanethionophosphonate of the formula

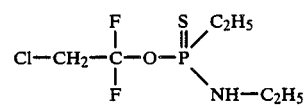

11. A pesticidal composition comprising a pesticidally effective amount of a compound according to claim 2 and a diluent.

12. A method of combating pests which comprises applying to such pests or to a pest habitat a pesticidally effective amount of a compound according to claim 1.

13. The method according to claim 12, wherein such compound is
O-ethyl O-(2-chloro-1,1-difluoro-ethyl) ethanethionophosphonate,
O-(2-chloro-1,1-difluoro-ethyl) propylamidoethanethionophosphonate,
O-(2-chloro-1,1-difluoro-ethyl) isopropylamidoethanethionophosphonate,
O-(2-chloro-1,1-difluoro-ethyl) isopropylamidomethanethionophosphonate,
O-(2-chloro-1,1-difluoro-ethyl) allylamidoethanethionophosphonate, or
O-(2-chloro-1,1-difluoro-ethyl) ethylamidoethanethionophosphonate.

* * * * *